United States Patent [19]

Bodmer et al.

[11] Patent Number: 5,639,480
[45] Date of Patent: Jun. 17, 1997

[54] SUSTAINED RELEASE FORMULATIONS OF WATER SOLUBLE PEPTIDES

[75] Inventors: David Bodmer, Klingnau, Switzerland; Jones W. Fong, Parsippany, N.J.; Thomas Kissel, Staufen, Germany; Hawkins V. Maulding, Mendham, N.J.; Oskar Nagele, Sissach, Switzerland; Jane E. Pearson, Ogendensburg, N.J.

[73] Assignee: Sandoz Ltd., Basel, Switzerland

[21] Appl. No.: 470,072

[22] Filed: Jun. 6, 1995

Related U.S. Application Data

[63] Continuation of Ser. No. 643,880, Jan. 18, 1991, Pat. No. 5,538,739, which is a continuation-in-part of Ser. No. 411,347, Sep. 22, 1989, abandoned, which is a continuation-in-part of Ser. No. 377,023, Jul. 7, 1989, abandoned.

[30] Foreign Application Priority Data

Jun. 25, 1990 [HU] Hungary ................................. 3974/90

[51] Int. Cl.⁶ ................................. A61K 9/14
[52] U.S. Cl. ..................... 424/501; 424/486; 424/426
[58] Field of Search ..................... 424/499, 501, 424/486, 426; 514/11; 530/311

[56] References Cited

U.S. PATENT DOCUMENTS

| | | | |
|---|---|---|---|
| 4,650,787 | 3/1987 | Schally et al. | 514/11 |
| 4,675,189 | 6/1987 | Kent et al. | 424/490 |
| 4,759,577 | 7/1988 | Schally et al. | 914/11 |
| 4,767,628 | 8/1988 | Hutchinson | 424/426 |
| 4,853,226 | 8/1989 | Machida et al. | 424/426 |
| 4,859,763 | 8/1989 | Takayanagi et al. | 424/426 |
| 4,863,736 | 9/1989 | Azain et al. | 424/426 |

FOREIGN PATENT DOCUMENTS

| | | |
|---|---|---|
| 0052510 | 5/1982 | European Pat. Off. . |
| 0058481 | 8/1982 | European Pat. Off. . |
| 0092918 | 11/1983 | European Pat. Off. . |
| 0203031 | 11/1986 | European Pat. Off. . |
| 2842089 | 4/1979 | Germany . |
| 2145422 | 3/1985 | United Kingdom . |
| 2208200 | 3/1989 | United Kingdom . |
| 2209937 | 6/1989 | United Kingdom . |
| 2234169 | 1/1991 | United Kingdom . |

OTHER PUBLICATIONS

Mason–Garcia, Proc. National Acad. Science, vol. 85, pp. 5688–5692 (1988).

Maulding, Journal of Controlled release, vol. 6, pp. 167–176 (1987).

*Primary Examiner*—Edward J. Webman
*Attorney, Agent, or Firm*—Robert S. Honor; Carl W. Battle

[57] ABSTRACT

The invention discloses microparticles comprising a polypeptide, preferably somatostatin or an analog or derivative thereof, more preferably octreotide, in a polymeric matrix, preferably poly(lactide-co-glycolide)glucose. The invention also discloses sustained release formulations containing said microparticles and the use of said formulations in treating acromegaly and breast cancer.

13 Claims, No Drawings

SUSTAINED RELEASE FORMULATIONS OF WATER SOLUBLE PEPTIDES

This is a continuation of application Ser. No. 07/643,880, filed Jan. 18, 1991, now U.S. Pat. No. 5,538,739, which in turn is a continuation-in-part of application Ser. No. 07/411,347, filed Sep. 22, 1989, which in turn is a continuation-in-part of application Ser. No. 07/377,023, filed Jul. 7, 1989, the latter two of which are now abandoned.

BACKGROUND OF THE INVENTION

This invention relates to sustained release (depot) formulations of drugs in particular water soluble peptides, e.g. somatostatin or somatostatin analogs, such as octreotide, in a biodegradable and biocompatible polymeric carrier, e.g. a matrix or a coating, e.g. in the form of a implant or preferably a microparticle (also known as a microcapsule or a microsphere).

The invention also relates to such formulations, showing satisfactory peptide release profiles over a particular period of time.

Peptide drugs often ahoy after oral or parenteral administration a poor bioavailability in the blood, e.g. due to their short biological half-lives caused by their metabolic instability. If orally or nasally administered they additionally often show a poor resorption through the mucuous membranes. A therapeutically relevant blood level over an extended period of time is difficult to achieve.

The parenteral administration of peptide drugs as a depot formulation in a biodegradable polymer, e.g. as microparticles or implants, has been proposed enabling their sustained release after a residence time in the polymer which protects the peptide against enzymatic and hydrolyric influences of the biological media.

Although some parenteral depot formulations of peptide drugs in a polymer in the form of microparticles or an implant, are known, satisfactory peptide release profiles are in practice only obtained in very few cases. Special measures must be taken to achieve a continuous peptide release for a therapeutically active drug serum level and if desired avoiding too high drug serum concentrations, which cause undesired pharmacological side reactions.

The peptide drug release pattern is dependent on numerous factors, e.g. the type of the peptide, and e.g. whether it is present in its free or in another form, e.g. salt form, which may influence its water solubility. Another important factor is the choice of polymer, from the extended list of possibilities which have been described in the literature.

Each polymer type has its characteristic biological degradation rate. Free carboxyl groups may be formed which contribute to the pH value in the polymer and thus additionally influence the water solubility of the peptide and thus its release pattern.

Other factors, which may influence the release pattern of the depot formulation, are the drug loading of its polymeric carrier, the manner of its distribution in the polymer, the particle size and, in case of an implant, additionally its shape. Further is the site of the formulation in the body of influence.

Until now no somatostatin composition in sustained release form for parenteral administration has reached the market, perhaps because no composition exhibiting a satisfactory serum level profile could be obtained.

DESCRIPTION OF TEE PRIOR ART

Polymer formulations with drugs which are designed to give prolonged or delayed release of the drug are known in the art.

U.S. Pat. No. 3,773,919 discloses controlled drug release formulations in which the drug, e.g. a water soluble peptide drug is dispersed in a biodegradable and biocompatible linear polylactide or polylactide-co-glycolide polymer. However, no drug release patterns have been described and there is no reference to a somatostatin. U.S. Pat. 4,293,539 describes anti-bacterial formulations in microparticle form.

U.S. Pat. No. 4,675,189 describes sustained release formulations of the LHRH analog decapeptide nafareline and analogous LHRH congeners in polylactide-co-glycolide polymers. No release pattern has been described.

T. Chang, J. Bioeng., Vol.1, pp.25–32, 1976 described prolonged release of biologicsis, enzymes and vaccines from microparticles. Polymers/copolymers of lactic acid and lactide/glycolide copolymers and related compositions for use in surgical applications and for sustained release and biodegradation have been reported in U.S. Pat. Nos. 3,991,776; 4,076,798 and 4,118,470.

European patent application 0 203 031 describes a series of somatostatin octapeptide analogs, e.g. Compound RC-160 having the formula:

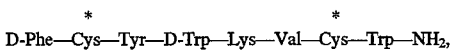

$$\text{D-Phe—Cys—Tyr—D-Trp—Lys—Val—Cys—Trp—NH}_2,$$

having a bridge between the -Cys- moieties, in columns 15–16.

The possibility of the somatostatins being microencapsulated with polylactide-co-glycolide polymer has been mentioned in claim 18, but no instructions have been disclosed how to obtain a continuous therapeutically active serum level.

U.S. Pat. No. 4,011,312 describes that a continuous release of an antimicrobial drug, e.g. the water soluble polymyxin B from a polylactide-co-glycolide matrix of a low molecular weight (below 2000) and a relatively high glycolide content in the form of an implant, can be obtained, when the implant is inserted into the teat canal of a cow. The drug is released within a short period of time, due to the high glycolide content and the low molecular weight of the polymer, which both stimulate a quick polymer biodegradation and thus a corresponding quick release of the drug. A relatively high drug loading content additionally contributes to a quick drug release. No somatostatins and no drug release patterns have been described.

European Patent No. 58481 discloses that a continuous release of a water soluble peptide from a polylactide polymer implant is stimulated by lowering the molecular weight of at least a part of the polymer molecules, by introducing glycolide units into the polymer molecule, by increasing the block polymer character of the polymer when polylactide-co-glycolide molecules are used, by increasing the drug loading content of the polymer matrix and by enlarging the surface of the implant.

Although somatostatins are mentioned as water soluble peptides, no somatostatin release profiles have been described and no indication has been given how to combine all these parameters to obtain e.g. a continuous somatostatin serum level over at least one week, e.g. one month.

European Patent No. 92918 describes that a continuous release of peptides, preferably of hydrophilic peptides, over an extended period of time can be obtained, when the peptide is incorporated in a conventional hydrophobic polymer matrix, e.g. of a polylactide, which is made more accessible for water by introducing in its molecule a hydrophilic unit, e.g. of polyethyleneglycol, polyvinylalcohol, dextran or polymethacrylamide. The hydrophilic contribution to the amphipathic polymer is given all the ethylene oxide groups in case of a polyethylene glycol unit, by the free hydroxyl groups in the case of a polyvinylalcohol unit or of a dextran unit, and by the amide groups in the case of a polymethyacrylamide unit. Due to the presence of the hydrophilic unit in the polymer molecules the implant will obtain hydrogel properties after the absorption of water. Somatostatin is mentioned as an hydrophilic peptide, but no release profile has been described and no indication has been given, what type of polymer is preferred for this peptide, and what molecular weight and how many hydrophilic groups it should have.

GB 2,145,422 B describes that a sustained release of drugs of several types, e.g. of vitamins, enzymes, antibiotics, antigens, can be obtained over an extended period of time, when the drug is incorporated in an implant, e.g. of microparticle size, made of a polymer of a polyol, e.g. glucose or mannitol, having one or more, preferably at least 3, polylactide ester groups. The polylactide ester groups preferably contain e.g. glycolide units. No peptides, e.g. somatostatins, are mentioned as drugs and no serum drug levels have been disclosed.

SUMMARY OF THE INVENTION

This invention relates to sustained release formulations, e.g. microparticle formulations, of a drug, especially of a hormonally active water-soluble somatostatin or a somatostatin analog such as octreotide, providing a satisfactory drug plasma level and, e.g. in a biodegradable, biocompatible polymer, e.g. in a encapsulating polymer matrix. The polymer matrix may be a synthetic or natural polymer.

The microparticles of this invention may be prepared by any conventional technique, e.g. an organic phase separation technique, a spray drying technique or a triple emulsion technique, wherein the polymer is precipitated together with the drug, followed by hardening of the resulting product, when the phase separation or triple emulsion technique are used.

If desired the sustained release formulations may be in the form of an implant.

We have found an especially useful modification of the phase separation technique for preparing microparticles of any drug.

Accordingly the present invention also provides a process for the production of a microparticle comprising a drug in a biodegradable, biocompatible carrier which comprises the steps of:
a) dissolving the polymeric carrier material in an appropriate solvent, in which the drug compound is not soluble.
b) adding and dispersing a solution of the drug compound in an appropriate solvent, e.g. an alcohol, which is a non-solvent for the polymer, in the solution of step a),
c) adding a phase inducing agent to the dispersion of step b), to induce microparticle formation,
d) adding the mixture of step c) to an oil-in-water emulsion to harden the microparticle, and
e) recovering the microparticle.

We have also found an especially useful modification of the triple emulsion technique for preparing microparticles of any drug.

Accordingly the present invention provides:
A process for producing microparticles which comprises
(i) intensively mixing a water-in-oil emulsion formed from an aqueous medium and a water-immiscible organic solvent containing in one phase the drug and in the other a biodegradable, biocompatible polymer, with an excess of an aqueous medium containing an emulsifying substance or a protective colloid to form a water-in-oil-in-water emulsion, without adding any drug retaining substance to the water-in-oil emulsion or applying any intermediate viscosity increasing step,
ii) desorbing the organic solvent therefrom, and
iii) isolating and drying the resultant microparticles.

The present invention additionally provides the microparticles obtained according to these processes.

The present invention also provides:
a) a sustained release formulation comprising a peptide drug compound in a 40/60 to 60/40 polylactide-co-glycolide ester of a polyol, the polyol unit chosen from the group of a ($C_{3-6}$) carbon chain containing alcohol having 3 to 6 hydroxyl groups and a mono- or di-saccharide, and the esterified polyol having at least 3 polylactide-co-glycolide chains.

b) A sustained release formulation comprising a peptide drug compound chosen from the group of a calcitonin, lypressin or a somatostatin in a 40/60 to 60/40 polylactide-co-glycolide polymer having linear chains of a molecular weight $M_w$ between 25,000 and 100,000, a polydispersity $M_w/M_n$ between 1.2 and 2 in a concentration of from 0.2, preferably 2 to 10% of weight of the peptide drug compound therein.

c) A sustained release formulation comprising octreotide or a salt or a derivative thereof in a biodegradable, biocompatible polymeric carrier.

We have found that a novel salt of octreotide is the pamoate which is very stable in such formulations. The present invention accordingly provides (i) octreotide pamoate and (ii) a process for the production of octreotide pamoate which comprises reacting octreotide with embonic acid (or a reactive derivative thereof).

Additionally the present invention provides:
A method of administering a peptide to a subject which comprises administering parenterally to a subject in need of such treatment a depot formulation as defined above, especially for the treatment of acromegaly or breast cancer.

DESCRIPTION OF THE PREFERRED EMBODIMENTS

The drugs of use in the processes of the invention are preferably water soluble drugs, e.g. peptides.

The peptides of use in the processes and formulations of this invention may be a calcitonin, such as salmon calcitonin, lypressin, and the naturally occuring somatostatin and synthetic analogs thereof.

The naturally occuring somatostatin is one of the preferred compounds and is a tetradecapeptide having the structure:

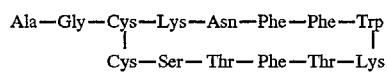

This hormone is produced by the hypothalmus gland as well as other organs, e.g. the GI tract, and mediates, together with GRF, q.v. the neuroregulation of pituitary growth hormone release. In addition to inhibition of GH release by the pituitary, somatostatin is a potent inhibitor of a number of systems, including central and peripheral neural, gastrointestinal and vascular smooth muscle. It also inhibits the release of insulin and glucagon.

The term "somatostatin" includes its analogues or derivatives thereof. By derivatives and analogues is understood straight-chain, bridged or cyclic polypeptides wherein one or more amino acid units have been omitted and/or replaced by one or more other amino radical(s) of and/or wherein one or more functional groups Have been replaced by one or more other functional groups and/or one or more groups have been replaced by one or several other isosteric groups. In general, the term covers all modified derivatives of a biologically active peptide which exhibit a qualitatively similar effect to that of the unmodified somatostatin peptide.

Agonist analogs of somatostatin are thus useful in replacing natural somatostatin in its effect on regulation of physiologic functions.

-continued (D)Ala—Cys—Tyr—(D)Trp—Lys—Val—Cys—ThrNH$_2$ g) (D)Phe—Cys—Tyr—(D)Trp—Lys—Val—Cys-β-Nal—NH$_2$ h) 3-(2-(naphthyl)-

Ala—Cys—Tyr—(D)Trp—Lys—Val—Cys-β-Nal—NH$_2$ i) (D)Phe—Cys-β-Nal—(D)Trp—Lys—Val—Cys—Thr—NH$_2$ wherein in each of compounds a) to i) there is a bridge between the amino acids marked with a * as indicated in the next formula.

Other preferred somatostatins are:

H—Cys—Phe—Phe—(D)Trp—Lys—Thr—Phe—Cys—OH (See Vale et al., Metabolism, 27, Supp.1, 139 (1978)).

Asn—Phe—Phe—(D)Trp—Lys—Thr—Phe—Gaba (See European Pat. Publication No. 1295 and Appln. No. 78 100 994.9).

MeAla—Tyr—(D)Trp—Lys—Val—Phe (See Verber et al., Life Sciences, 34, 1371-1378 (1984) and European Pat. Appln. No. 82106205.6 (published as No. 70 021)) also known as cyclo (N—Me—Ala—Tyr—D-Trp—Lys—Val—Phe).

NMePhe—His—(D)Trp—Lys—Val—Ala (See R.F. Nutt et al.,. Klin. Wochenschr. (1986) 64 (Suppl. VII)

H—Cys—His—His—Phe—Phe—(D)Trp—Lys—Thr—Phe—Thr—Ser—Cys—OH (see EP-A-200, 188).

X—Cys—Phe—D-Trp—Lys—Thr—Cys—Thr—NH$_2$
and

X—Cys—Phe—D-Trp—Lys—Thr—Cys—Thr—ol wherin X is a cationic anchor especially

Ac—hArg(Et$_2$)—Gly—Cys—Phe—D-Trp—Lys—Thr—Cys—NH$_2$ (See EP 0363589A2)

Preferred known somatostatins are:

a) (D)Phe—Cys—Phe—(D)Trp—Lys—Thr—Cys—Thr—ol
(Generic name Octreotide)

b) (D)Phe—Cys—Tyr—(D)Trp—Lys—Val—Cys—ThrNH$_2$ c) (D)Phe—Cys—Tyr—(D)Trp—Lys—Val—Cys—TrpNH$_2$ d) (D)Trp—Cys—Phe—(D)Trp—Lys—Thr—Cys—ThrNH$_2$ e) (D)Phe—Cys—Phe—(D)Trp—Lys—Thr—Cys—ThrNH$_2$ f) 3-(2-(Naphthyl)- wherein in the above mentioned amino acids there is a bridge between the amino acids marked with a *.

The contents of all the above publications including the specific compounds are specifically incorporated herein by reference.

The term derivative includes also the corresponding derivatives bearing a sugar residue.

When somatostatins bear a sugar residue, this is preferably coupled to a N-terminal amino group and/or to at least one amino group present in a peptide side chain, more preferably to a N-terminal amino group. Such compounds and their preparation are disclosed, e.g. in WO 88/02756.

The term octreotide derivatives includes those including the moiety

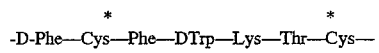

-D-Phe—Cys—Phe—DTrp—Lys—Thr—Cys— having a bridge between the Cys residues.

Particularly preferred derivatives are $N^\alpha$-[α-glucosyl-(1-4-deoxyfructosyl]-DPhe-Cys-Phe-DTrp-Lys-Thr-Cys-Thr-ol and $N^\alpha$-[β-deoxyfructosyl-DPhe-Cys-Phe-DTrp-Lys-Thr-Cys-Thr-ol, each having a bridge between the -Cys-moieties, preferably in acetate salt form and described in Examples 2 and 1 respectively of the above mentioned application.

The somatostatins may exist e.g. in free form, salt form or in the form of complexes thereof. Acid addition salts may be formed with e.g. organic acids, polymeric acids and inorganic acids. Acid addition salts include e.g. the hydrochloride and acetates. Complexes are e.g. formed from somatostatins on addition of inorganic substances, e.g. inorganic salts or hydroxides such as Ca- and Zn-salts and/or an addition of polymeric organic substances.

The acetate salt is a preferred salt for such formulations, especially for microparticles leading to a reduced initial drug burst. The present invention also provides the pamoate salt, which is useful, particularly for implants and the process for its preparation. The pamoate may be obtained in conventional manner, e.g. by reacting embonic acid (pamoic acid) with octreotide e.g. in free base form. The reaction may be effected in a polar solvent, e.g. at room temperature.

The somatostatins are indicated for use in the treatment of disorders wherein long term application of the drug is envisaged, e.g. disorders with an aetiology comprising or associated with excess GH-secretion, e.g. in the treatment of acromegaly, for use in the treatment of gastrointestinal disorders, for example, in the treatment or prophylaxis of peptic ulcers, enterocutaneous and pancreaticocutaneous fistula, irritable bowel syndrome, dumping syndrome, watery diarrhea syndrome, acute pancreatitis and gastroenteropathic endocrine tumors (e.g. vipomas, GRPomas, glucagonomas, insulinomas, gastrinomas and carcinoid tumors) as well as gastro-intestinal bleeding, breast cancer and complications associated with diabetes.

The polymeric carrier may be prepared from biocompatible and biodegradable polymers, such as linear polyesters, branched polyesters which are linear chains radiating from a polyol moiety, e.g. glucose. Other esters are those of polylactic acid, polyglycolic acid, polyhydroxybutyric acid, polycaprolactone, polyalkylene oxalate, polyalkylene glycol esters of acids of the Kreb's cycle, e.g. citric acid cycle and the like and copolymers thereof.

The preferred polymers of this invention are the linear polyesters, and the branched chain polyesters. The linear polyesters may be prepared from the alphahydroxy carboxylic acids, e.g. lactic acid. and glycolic acid, by the condensation of the lactone dimers, see for example U.S. Pat. No. 3,773,919.

Linear polylactide-co-glycolides which are preferably used according to the invention conveniently have a molecular weight between 25,000 and 100,000 and a polydispersibility Mw/Mn e.g. between 1.2 and 2.

The branched polyesters preferably used according to the invention may be prepared using polyhydroxy compounds e.g. polyol e.g. glucose or mannitol as the initiator. These esters of a polyol are known and described in GB 2,145,422 B. The polyol contains at least 3 hydroxy groups and has a molecular weight of up to 20,000, with at least 1, preferably at least 2, e.g. as a mean 3 of the hydroxy groups of the polyol being in the form of ester groups, which contain poly-lactide or co-poly-lactide chains. Typically 0.2% glucose is used to initiate polymerization. The structure of the branched polyesters is star shaped. The preferred polyester chains in the linear and star polymer compounds preferably used according to the invention are copolymers of the alpha carboxylic acid moieties, lactic acid and glycolic acid, or of the lactone dimers. The molar ratios of lactide: glycolide is from about 5:25 to 25:75, e.g. 60:40 to 40:60, with from 55:45 to 45:55, e.g. 55:45 to 50:50 the most preferred.

The star polymers may be prepared by reacting a polyol with a lactide and preferably also a glycolide at an elevated temperature in the presence of a catalyst, which makes a ring opening polymerization feasible.

We have found that an advantage of the star polymer type in the formulations of the present invention is, that its molecular weight can be relatively high, giving physical stability, e.g. a certain hardness, to implants and to microparticles, which avoids their sticking together, although relatively short polylactide chains are present, leading to a controllable biodegradation rate of the polymer ranging from several weeks to one or two months and to a corresponding sustained release of the peptide, which make a depot formulation made therefrom suitable for e.g. a one month's release.

The star polymers preferably have a main molecular weight $M_w$ in the range of from about 10,000 to 200,000, preferably 25,000 to 100,000, especially 35,000 to 60,000 and a polydispersity e.g. of from 1.7 to 3.0, e.g. 2.0 to 2.5. The intrinsic viscosities of star polymers of $M_w$ 35,000 and $M_w$ 60,000 are 0.36 resp. 0.51 dl/g in chloroform. A star polymer having a $M_w$ 52;000 has a viscosity of 0.475 dl/g in chloroform.

The terms microsphere, microcapsule and microparticle are considered to be interchangeable with respect to the invention, and denote the encapsulation of the peptides by the polymer, preferably with the peptide distributed throughout the polymer, which is then a matrix for the peptide. In that case preferably the terms microsphere or more generally microparticle are used.

Using the phase separation technique of the present invention the formulations of this invention may be prepared for example by dissolving the polymeric carrier material in a solvent, which is a nonsolvent for the peptide, following by the addition and dispersing a solution of the peptide in the polymer-solvent composition. A phase inducer e.g. a silicone fluid is then added to induce encapsulation of the peptide by the polymer.

The drug burst effect can be significantly reduced by in situ precipitation of ultra fine drug particles, by adding a drug solution to the polymer solution prior to phase separation. The prior art method involves adding dry particles directly to the polymer solution.

The therapeutic duration of peptide release can be increased by hardening/washing the microparticles with an emulsion of buffer/heptane. The prior art method involves a hardening step followed by either no subsequent washing, or a separate aqueous washing step.

An emulsion of the type oil-in-water ($=^o/_w$) may be used to wash and harden the microspheres and remove non-encapsulated peptide. The wash aids in the removal of non-encapsulated peptide from the surface of the microspheres. The removal of excess peptide from the microspheres diminishes the initial drug burst, which is characteristic of many conventional encapsulation formulations. Thus, a more consistent drug delivery over a period of time is possible with the present microsphere formulations.

The emulsion also aids in the removal of residual polymer solvent and the silicone fluid. The emulsion may be added to the polymer peptide mixture, or the mixture added to the emulsion. It is preferred that the polymer peptide mixture be added to the emulsion.

The o/w emulsion may be prepared using a emulsifier such as sorbitan mono-oleate (Span 80 ICI Corp.) and the like, to form a stable emulsion. The emulsion may be buffered with a buffer which is non-detrimental to the peptide and the polymer matrix material. The buffer may be from pH 2 to 8 with a pH 4 preferred. The buffer may be prepared from acidic buffers such as phosphate buffer, acetate buffer and the like. Water alone may be substituted for the buffer.

Heptane, hexane and the like may be used as the organic phase of the buffer.

The emulsion may contain dispersing agents such as silicone oil.

A preferred emulsion may comprise heptane, pH 4 phosphate buffer, silicone oil and sorbitan mono-oleate. When an initial drug release may be desirable, a single non-solvent hardening step may be substituted for the emulsion hardening. Heptane, hexane and the like, may be used as the solvent.

Other alternatives to the o/w emulsion may be used for hardening the microcapsules, such as:

Solvent plus emulsifier for hardening the microcapsules without washing; and solvent plus emulsifier for hardening followed by a separate washing step.

The o/w emulsion may be used without the dispersing agent. The dispersing agent, however, avoids aggregation of the dry particles of microcapsules due to static electricity, and helps to reduce the level of residual solvent.

Examples of the solvent for the polymer matrix material include methylene chloride, chloroform, benzene, ethyl acetate, and the like. The peptide is preferably dissolved in an alcoholic solvent, e.g. methanol, which is miscible with the polymer solvent.

The phase inducers (coacervation agents) are solvents which are miscible with the polymer-drug mixture, and cause the embryonic microcapsules to form prior to hardening; silicone oils are the preferred phase inducers.

The o/w emulsion may be prepared in a conventional manner using heptane, hexane and the like for the organic phase.

The microparticles of this invention may also be prepared by the generally known spray-drying procedure. According to this method the somatostatin, or a solution of the peptide in an organic solvent, e.g. methanol, in water or in a buffer, e.g of pH 3-8 and a solution of the polymer in an organic solvent, not miscible with the former one, e.g. methylene chloride, are thoroughly mixed.

The formed solution, suspension or emulsion is then sprayed in a stream of air, preferably of warm air. The generated microparticles are collected, e.g. by a cyclon and if desired washed, e.g. in a buffer solution of e.g. pH 3.0 to 8.0 preferably of pH 4.0 or distilled water and dried in a vacuum e.g. at a temperature of 20° to 40° C. The washing step can be applied, if the particles exhibit a drug burst in vivo, and the extent of the drug burst would be undesired. As a buffer an acetate buffer can be used.

Microparticles can accordingly be obtained, exhibiting an improved somatostatin release profile in vivo.

The invention thus also relates to the microparticles prepared by this process. The invention thus additionally provides a sustained release formulation prepared by mixing a somatostatin or a solution of a somatostatin in methanol or water or a buffer of pH 3-8 and a solution of the polylactide-co-glycolide in methylene chloride and spraying the formed solution, emulsion or suspension of somatostatin in the polymer solution in a stream of warm air, collecting the microspheres and washing them in a buffer solution of pH 3.0 to 8.0 or distilled water and drying them in a vacuum at a temperature of from 20 to 40° C. Compared with microparticles, prepared according to the phase separation technique, they do not contain silicon oil, even not in traces, since no silicon oil is used in the spray drying technique.

The formulations of the invention may also be prepared using a triple-emulsion procedure. In a typical technique, peptide e.g. octreotide is dissolved in a suitable solvent e.g. water and emulsified intensively into a solution of the polymer, e.g. 50/50 poly(D,L-lactide-co-glycolide)glucose in a solvent, which is a non-solvent for the peptide, e.g. in methylene chloride. Examples of the solvent for the polymer matrix material include methylene chloride, chloroform, benzene, ethyl acetate, and the like. The resulting water/oil (W/O) emulsion is further emulsified into an excess of water, containing an emulsifying substance, e.g. an anionic or non-ionic surfactant or lecithin or a protective colloid e.g. gelatine, dextrin, carboxymethylcellulose, polyvinylpyrrolidone or polyvinyl alcohol, which provides continuous generation of the triple (w/o/w) emulsion. The microparticles are formed by spontaneous precipitation of the polymer and hardened by evaporation of the organic solvent. Gelatine serves to prevent agglomeration of the microspheres. After sedimentation of the microparticles the supernatent is decanted and the microparticles are washed with water and then with acetate buffer. The microparticles are then filtered and dried.

The peptide can also be dispersed directly in the polymer solution, whereafter the resulting suspension is mixed with the gelatine containing water phase.

The triple emulsion procedure is known from the U.S. Pat. No. 4,652,441. According to this patent in a first step a drug solution (1) in a solvent, e.g. somatostatin in water (Column 2, lines 31-32), is thoroughly mixed with an excess of a polylactide-co-glycolide solution (2) in another solvent, in which the first solvent is not soluble, e.g. methylene chloride, giving a water-in-oil type ($^w/_o$) emulsion (3) of fine drug-containing droplets of (1) in solution(2).

In solution (1) is additionally dissolved a so-called drug-retaining substance (Column 1, line 31), e.g. gelatin, albumin, pectin, or agar.

In a second step, the viscosity of the inner phase (1) is increased by appropriate means, like heating, cooling, pH change, addition of metal ions, or cross linking of e.g. gelatin with an aldehyde.

In a third step, an excess of water is thoroughly mixed with the $^w/_o$-emulsion (3), (Column 7, lines 52-54), leading to a $^w/_o/_w$-type ternary-layer emulsion. In the excess of water a so-called emulsifying agent may if desired be present (Column 7, line 56), chosen from the group of e.g. an anionic or nonionic surfactant or e.g. polyvinyl pyrrolidone, polyvinyl alcohol or gelatine.

In a fourth step, the $^w/_o/_w$-emulsion is subjected to "in-water drying", (line 52). This means that the organic solvent in the oil layer is desorbed to generate microparticles. The desorption is accomplished in a manner known per se (Column 8, lines 3-5), e.g. by pressure decrease while stirring (Column 8, lines 5-7) or e.g. by blowing nitrogen gas through the oil layer (e.g. methylene chloride) (line 19).

The formed microparticles are recovered by centrifugation or filtration (lines 26-27) and the components which are not incorporated in the polymer are removed by washing with water (line 29). If desired, the microparticles are warmed under reduced pressure to achieve) better removal of water and of solvent (e.g. methylene chloride from the microparticle wall (lines 30-32).

Whilst the above process is satisfactory for the production of formulations according to the invention, however, the so-called drug-retaining substance mentioned above, e.g. gelatine, albumin, pectin or agar, is still enclosed in the resultant microparticles.

We have now found that when the addition of the drug retaining substance (=in solution (1)) and the step of increasing the viscosity of the inner phase is avoided, and in the excess of water of the ternary $^w/_o/_w$-emulsion, the measure of adding an emulsifying substance or a protective colloid, like gelatine is maintained, satisfactory microparticles can still be obtained. Additionally, the microparticles do not contain any drug retaining substance, and only a very small quantity of methylene chloride.

Therefore the invention provides a process for the production of microparticles prepared by intensively mixing:

a) a solution of a drug, preferably a somatostatin, especially octreotide in an aqueous medium, preferably water or a buffer, preferably in a weight/volume ratio of 0.8 to 4.0 g/1 to 120 ml, especially 2.5/10 and in a buffer of pH 3–8, especially an acetate buffer, and b) a solution of a polymer, preferably a polylactide-coglycolide, such as mentioned above, in an organic solvent, not miscible with the aqueous medium, e.g. methylene chloride, preferably in a weight/volume ratio of 40 g/90 to 400 ml, especially 40/100, preferably in such a manner that the weight/weight ratio of the drug to the polymer is from 1/10 to 50, especially 1/16 and the volume/volume ratio of the aqueous medium/ organic solvent is 1/1.5 to 30, especially 1/10, intensively mixing the $^w/_o$-emulsion of a) in b) together with c) an excess of an aqueous medium, preferably water or a buffer, e.g. an acetate or phosphate buffer, preferably of a pH 3–8, containing an emulsifying substance or a protective colloid, preferably in a concentration of 0.01 to 15.0%, particularly gelatine, especially, in a concentration of 0.1 to 3 %, particularly 0.5% of weight, preferably at a volume/volume mixing speed ratio of ab)/c) of from 1/10 to 100, especially 1/40, without adding any drug retaining substance to the water-in-oil emulsion or applying any intermediate viscosity increasing step, hardening the embryonic microparticles in the formed $^w/_o/_w$-emulsion by desorption, preferably by evaporation, of the organic solvent, preferably methylene chloride, and by isolating, optionally washing and drying the generated microparticles.

The invention also provides the process variant, in which the drug is dispersed directly in the polymer solution, whereafter the resulting dispersion is mixed with the gelatine containing water phase.

The invention also provides the microparticles produced by these processes. Like microparticles prepared according to the spray drying technique, they do not contain silicon oil. Compared with microparticles prepared according to the known triple emulsion process type, they do not contain any amount of a protective colloid.

The sustained release formulations can also be made by other methods known per se, e.g.

if the peptide is stable enough for the production of an implant, by heating microparticles containing the peptide, e.g. a somatostatin in a polylactide-coglycolide, especially such as described above or a mixture thereof obtained,by mixing the peptide and the polymer, at a temperature of e.g. from 70° to 100° C. and extruding and cooling the compact mass, after which the extrudate is cut and optionally washed and dried.

Conveniently the formulations according to the invention produced under aseptic conditions.

The formulations according to the invention may be utilized in depot form, e.g. injectable microspheres or implants.

They may be administered in conventional manner, e.g. subcutaneous or intramuscular injection, e.g. for indications known for the drug contained therein.

The sustained release formulations containing octreotide may be administered for all the known indications of the octreotide or derivatives thereof, e.g. those disclosed in GB 2,199,829 A pages 89–96, as well as for acromegaly and for breast cancer.

The microparticles of this invention may have a size range from about 1 to 250 microns diameter, preferably 10 to 200, especially 10 to 130, e.g. 10 to 90 microns. Implants may be e.g. from about 1 to 10 cubic mm. The amount of drug i.e. peptide present in the formulation depends on the desired daily release dosage and thus on the biodegradation rate of the encapsulating polymer. The exact amount of peptide may be ascertained by bioavailability trials. The formulations may contain peptide in an amount from at least 0.2, preferably 0.5 to 20 per cent by weight relative to the polymeric matrix, preferably 2.0 to 10, especially 3.0 to 6% of weight.

The release time of the peptide from the microparticle may be from one or two weeks to about 2 months.

Conveniently the sustained release formulation comprises somatostatin; e.g. octreotide in a biodegradable biocompatible polymeric carrier which, when administered to a rat subcutaneously at a dosage of 10 mg somatostatin per kg of animal body weight, exhibits a concentration of a somatostatin in the blood plasma of at least 0.3 ng/ml and preferably less than 20 ng/ml during a 30 day term, or conveniently a 60 day's term.

Alternatively conveniently the sustained release formulation comprises a somatostatin, e.g. octreotide in a biodegradable biocompatible polymeric carrier, which, when administered to a rabbit intramuscularly at a dosage of 5 mg per kg of body weight, exhibits a concentration of a somatostatin of at least 0.3 ng/ml during a 50 day's term and conveniently a concentration of at most 20 ng/ml.

Further preferred properties of the obtained somatostatin, e.g. octreotide containing depot formulations are, depending on the used production processes:

| Phase separation technique | | |
|---|---|---|
| Rabbit 5 mg of somatostatin/kg, intramuscularly | | |
| retardation | (0–42 days) | 76% |
| average plasma level (cp, ideal) | (0–42 days) | 4 ng/ml |
| AUC | (0–42 days) | 170 ng/ml × days |
| Spray drying technique: | | |
| Rat 10 mg of somatostatin/kg, subcutaneously | | |
| retardation | (0–42 days) | >75% |
| average plasma level ($c_{p,ideal}$) | (0–42 days) | 4–6 ng/ml |
| AUC | (0–42 days) | 170–210 ng/ml × days |
| Rabbit 5 mg of somatostatin/kg, intramuscularly | | |
| retardation | (0–43 days) | >75% |
| average plasma level ($c_{p,ideal}$) | (0–43 days) | 4–6 ng/ml |
| AUC | (0–43 days) | 200–240 ng/ml × days |

Triple emulsion technique:

Rat 10 mg of somatostatin/kg, subcutaneously

| | | |
|---|---|---|
| retardation | (0–42 days) | >75% |
| average plasma level ($c_{p,ideal}$) | (0–42 days) | 4–6.5 ng/ml |
| AUC | (0–42 days) | 170–230 ng/ml × days |

Rabbit 5 mg of somatostatin/kg, intramuscularly

| | | |
|---|---|---|
| retardation | (0–42/43 days) | >74% |
| average plasma level ($c_{p,ideal}$) | (0–42/43 days) | 3.5–6.5 ng/ml |
| AUC | (0–42/43 days) | 160–270 ng/ml × days |

The invention thus also provides somatostatin preferably octreotide and octreotide analog compositions, having the following properties:

1. a retardation of at least 70%, preferably at least 74%, e.g. at least 75%, 80%, 88% or at least 89% over a period of from 0 to 42 or 43 days and/or
2. an average plasma level ($C_{p,ideal}$) of 2.5–6.5, preferably 4–6.5 ng/ml over a period of from 0 to 42 days, in the rat, when 10 mg of somatostatin is subcutaneously administered and/or an average plasma level of 3.5–6.5, e.g. 4–6.5 ng/ml over a period of from 0 to 42 or 43 days in the rabbit when 5 mg of somatostatin is intramuscularly administered and/or
3. an AUC over a period of from 0 to 42 days of at least 160, preferably of from 170–230 ng/ml×days, for the rat, when 10 mg of somatostatin is subcutaneously administered and/or an AUC over a period of from 0 to 42 or 43 days of at least 160, preferably of from 180 to 275, e.g. from 200 to 275 ng/ml×days for the rabbit, when 5 mg of somatostatin is intramuscularly administered.

For the quantitative characterization of the sustained release formulations described above we use the method of area deviation (AD) published by F. Nimmerfall and J. Rosenthaler; Intern. J.Pharmaceut. 32, 1–6 (1986). In brief, the AD method calculates the area deviations of the experimental plasma profile from an ideal profile which is a constant average plasma level (=$C_{p,ideal}$) produced by conversion of the experimental area under the plasma level-time curve (AUC) to a rectangle of equal area. From the percental area deviation (referred to AUC) the % retardation is calculated as follows:

% retardation=100×(1−AD/AUC)

By this method the whole plasma profile measured over a preselected time period is characterized by means of a single numerical index.

In Proc. Natl. Acad. Sci. U.S.A. 85 (1988) 5688–5692 has been described in FIG. 4 a plasma level profile of the octapeptide analog of somatostatin of the formula

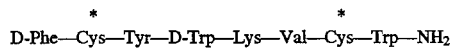

D-Phe—Cys—Tyr—D-Trp—Lys—Val—Cys—Trp—NH$_2$ in the rat.

However, a clear comparison can not be made with the plasma level data of the compositions of the invention in the rat, mentioned just before, since the described plasma level profile was based on another administration method (intramuscular injection) and—what is more important—the microcapsules' loading level (between 2 and 6%) and dosage amount for administration (25 to 50 mg portions of microcapsules for 30 days, although for at least during 45 days determinations were made) were not exactly indicated. Additionally the type of used poly(Dl-lactide-co-glycolide) was not exactly described.

The disclosure value of the publication is thus too low to admit it to be a prepublication, interfering with the invention.

The following examples illustrate the invention.

$M_w$ of polymers is the mean molecular weight as determined by GLPC using polystyrene as standard.

EXAMPLE 1

One g. of poly(D,L-lactide-co-glycolide)(50/50 molar, $M_w$=45,000; polydispersity ca. 1.7) was dissolved in 15 ml of methylene chloride with magnetic stirring followed by the addition of 75 mg of Octreotide acetate dissolved in 0.5 ml of methanol. Fifteen ml of silicon oil (brand Dow 360 Medical Fluid 1000 cs) (silicone fluid) was added to the polymer-peptide mixture. The resulting mixture was added to a stirred emulsion containing 400 ml n-heptane, 100 ml pH 4 phosphate buffer, 40 ml Dow 360 Medical Fluid, 350 cs and 2 ml Span 80 (emulsifier). Stirring was continued for a minimum of 10 minutes. The resulting microparticles were recovered by vacuum filtration and dried overnight in a vacuum oven. The yield was approximately 90% of microparticles in the 10 to 40 micron size range.

The microparticles were suspended in a vehicle and administered IM in a 4 mg dose of Octreotide to white New Zealand rabbits. Blood samples were taken periodically, indicating plasma levels of 0.5 to 1.0 ng/ml for 30 days as measured by Radioimmunoassay (RIA) analysis.

EXAMPLE 2

One g of poly(D,L-lactide-co-glycolide) glucose ($M_w$= 45,000 (55/45 molar produced according to the process of GB 2,145,422 B; polydispersity ca. 1.7; produced from 0.2% glucose) was dissolved in 25 ml of ethyl acetate with magnetic stirring followed by the addition of 75 mg of Octreotide dissolved in 3 ml of methanol. Twentyfive ml of silicon oil (brand Dow 360 Medical Fluid, 1000 cs) was added to the polymer-peptide mixture. The resulting mixture was added to the emulsion described in Example 1. Stirring was continued for a minimum of 10 minutes. The resulting microparticles were recovered by vacuum filtration and dried overnight in a vacuum oven. The yield was greater than 80% of microparticles in the 10 to 40 micron size range.

The microparticles were suspended in a vehicle and administered IM in a 4 mg dose of octreotide to white New Zealand rabbits. Blood samples were taken periodically indicating plasma levels of 0.5 to 2 ng/ml for 21 days as measured by RIA.

EXAMPLE 3

A solution of 1.5 g of Octreotide acetate in 20 ml of methanol was added with stirring to a solution of 18.5 g of poly(D,L-lactide-co-glycolide)glucose (50:50 molar, Mw 45,000) in 500 ml of methylene chloride. Phase separation was effected by adding 500 ml of Dow 360 Medilcal Fluid (1000 cs) and 800 ml of Dow 360 Medical Fluid (350 cs) to the peptide-polymer suspension. The resultant mixture was added to a stirred emulsion consisting of 1800 ml of n-heptane, 2000 ml of sterile water and 40 ml of Span 80. After stirring for 10 minutes, the microspheres were collected by vacuum filtration.

Half of the product was dried overnight in a vacuum oven at 37 C. The residual methylene chloride level was 1.2%.

The other half of the product was washed by stirring with 1000 ml of ethanol containing 1 ml of Span 80. After stirring for one hour, the ethanol was decanted and the microparticles were stirred with 1000 ml of n-heptane containing 1 ml of Span 80. After stirring for one hour, the microparticles were collected by vacuum filtration and dried overnight in a vacuum oven at 37° C. The residual methylene chloride level of the microparticles washed in this manner was reduced from 1.2% to 0.12%.

The combined yield of the product was 18.2 g (91%) of microparticles containing 5.6% Octreotide, mean diameter of 24 microns, 1.5% residual heptane.

The microparticles were suspended in a vehicle and injected intramuscularly in 5 mg/kg dose of Octreotide to white rabbits. Blood samples were taken periodically, indicating plasma levels of 0.3 to 7.7 ng/ml for 49 days as measured by RIA.

EXAMPLE 4

One g of poly (D.L,-lactide-co-glycolide)glucose $M_w$ 46,000 (50:50) molar produced according to the process of GB 2,145,422 B, Polydispersity ca. 1.7, produced from 0.2% glucose) was dissolved in 10 ml of methylene chloride with magnetic stirring followed by the addition of 75 mg of Octreotide dissolved in 0.133 ml of methanol. The mixture was intensively mixed e.g. by means of an Ultra-Turax for one minute at 20,000 rpm causing a suspension of very small crystals of Octreotide in the polymer solution.

The suspension was sprayed by means of a high speed turbine (Niro Atomizer) and the small droplets dried in a stream of warm air generating microparticles. The microparticles were collected by a "zyklon" and dryed overnight at room temperature in a vacuum oven.

The microparticles were washed with $1/15$ molar acetate buffer pH4.0 during 5 minutes and dried again at room temperature in a vacuum oven. After 72 hours the microparticles were sieved (0.125mm mesh size) to obtain the final product. The microparticles were suspended in a vehicle and administered i.m. in 5 mg/kg dose of Octreotide to white rabbits (chinchilla-bastard) and s.c. in a 10mg/kg dose to male rats. Blood samples were taken periodically, indicating plasma levels of 0.3 to 10.0 ng/ml (5 mg dose) in rabbits and 0.5 to 7.0 ng/ml in rats for 42 days as measured by Radioimmunoassay (RIA) analysis.

EXAMPLE 5

Microparticles were prepared by spray-drying in the same way as described for example 4 with the only change that Octreotide was suspended directly in the polymer solution, without use of methanol.

The microparticles were suspended in a vehicle and administered s.c. in a 10 mg/kg dose of Octreotide to male rats. Blood samples were taken periodically, indicating plasma levels of 0.5 to 10.0 ng/ml in rats for 42 days a$_s$ measured by Radioimmunoassay (RIA) analysis.

EXAMPLE 6

One g of poly(D.L,-lactide-co-glycolide)glucose, $M_w$ 46,000 (50:50 molar produced according to the process of GB 2,145,422 B, Polydispersity ca. 1.7, produced from 0.2% glucose) was dissolved in 2.5 ml of methylene chloride followed by the addition of 75 mg of Octreotide dissolved in 0.125 ml of deionized water. The mixture was intensively mixed e.g. by means of an Ultra-Turax for one minute at 20,000 rpm (inner W/O-phase).

One g of Gelatine A was dissolved in 200 ml of deionized water at 50° C. and the solution cooled down to 20° C. (outer W-phase). The W/O - and the W-phases were intensively mixed. Thereby the inner W/O-phase was separated into small droplets which were dispersed homogenously in the outer W-phase. The resulting triple emulsion was slowly stirred for one hour. Hereby the methylene chloride was evaporated and the microcapsules were hardened from the droplets of the inner phase. After sedimentation of the microparticles the supernatant was sucked off and the microparticles were recovered by vacuum filtration and rinsed with water to eliminate gelatine. Drying, sieving, washing and secondary drying of the microparticles was done as described for example 4. The microparticles were suspended in a vehicle and administered i.m. in 5 mg/kg dose of Octreotide to white rabbits (chinchilla-bastard) and s.c. in a 10 mg/kg dose to male rats. Blood samples were taken periodically, indicating plasma levels of 0.3 to 15.0 ng/ml (5 mg dose) in rabbits and 0.5 to 8.0 ng/ml in rats for 42 days as measured by Radioimmunoassay (RIA) analysis.

EXAMPLE 7

Microparticles were prepared by the triple-emulsion technique in the same way as described for example 6 with three changes:

1. 0.25 ml of acetate buffer pH 4.0 were used instead of 0.125 ml of water to prepare the inner W/O-phase.
2. rinsing after collection of the microparticles was carried out with 1/45 molar acetate buffer pH 4.0 instead of water.
3. further washing of microparticles was omitted.

EXAMPLE 8

Microparticles were prepared by the triple-emulsion technique in the same way as described for example 7 with the only change that the inner W/O -phase was prepared by using water containing 0.7%(w/v) sodium chloride instead of acetate buffer.

EXAMPLE 9

Microparticles were prepared in the same manner as described in example 6, with the only difference, that the drug compound is dispersed directly in the polymer solution, whereafter the resulting dispersion is mixed with the gelatine containing water phase.

EXAMPLE 10

Octreotide pamoate 10.19 g of octreotide free base (10 mM) and 3.88 embonoic acid (10 mM) are dissolved in 1 liter of water/dioxane (1:1). The reaction mixture is filtered, and lyophilized to give a yellow powder $[\alpha]^{20}D=+7.5°$ (C=0.35, in DMF), of octreotide pamoate hydrate. Factor=1.4 wherein the factor=weight of lyophilizate/weight of octreotide contained therein.

The pamoate may replace the octreotide acetate present in the microparticles of Examples 1–9 and has an excellent stability.

EXAMPLE 11

A solution of 1 g of poly(D.L-lactide-co-glycolide) (50:50 molar, MW=36,100) in 20 ml of methylene chloride was added with stirring to a solution of 100 mg of calcitonin in 1.5 ml of methanol. Phase separation was effected by adding 20 ml of silicone fluid (Dow 360 Medical Fluid, 1000 cs). The resultant mixture was added to a stirred emulsion consisting of 100 ml of pH 4 phosphate buffer, 400 ml of n-heptane, 4 ml of Span 80, and 40 ml of silicone fluid (Dow 360 Medical Fluid, 1000 cs). After stirring for 10 minutes, the microspheres were collected by vacuum filtration and dried overnight in a vacuum oven at 37 C. The yield was 1.1 g of microspheres containing 5.9% calcitonin.

EXAMPLE 12

A solution of 9.9 g of poly(D,L-lactide-co-glycolide) (50/50 molar, Mw=44,300) in 140 ml of methylene chloride was added to 100 mg of lypressin. The dispersion was magnetically stirred for one hour before adding 140 ml of silicone fluid (Dow 360 Medical Fluid, 1000 cs) and 2.5 ml of Span 80. The mixture was added to 2000 ml of heptane and stirred for 10 minutes. The resulting microcapsules were collected by vacuum filtration, washed three times with heptane, and dried 10 minutes under suction. Half of the sample was washed by stirring in water for 10 minutes; the other half was not washed. Both samples were dried overnight in a vacuum oven at 30 C. The total yield was 10.65 g of microcapsules. Analysis of the washed sample was 0.5% lypressin and 0.6% for the sample not washed with water.

What is claimed is:

1. A microparticle having a diameter of between 1 and 250 microns comprising octreotide, in a free base, acid addition salt or complex form in a biodegradable, biocompatible polymeric matrix of a 40/60 to 60/40 polylactide-co-glycolide ester of a polyol, said polyol being selected from the group consisting of 1) a ($C_{3-6}$) carbon chain containing alcohol having 3 to 6 hydroxyl groups, 2) a mono-saccharide and 3) a di-saccharide, and said esterified polyol having at least 3 polylactide-co-glycolide chains, wherein said octreotide is present in a therapeutically effective amount from at least 0.2 percent by weight relative to said polymeric matrix and said octreotide is distributed throughout said polymeric matrix.

2. A microparticle according to claim 1 wherein the octreotide is in a polymeric matrix of poly(D,L-lactide co-glycolide)glucose.

3. A sustained release formulation comprising a microparticle of claim 2.

4. A sustained release formulation according to claim 3 which when administered subcutaneously to a rat at a dosage of 10 mg of octreotide per kg of body weight exhibits an octreotide concentration in the blood plasma of at least 0.3 ng/ml and less than 20 ng/ml during a 30 day term.

5. A sustained release formulation according to claim 3 which when administered to a rabbit intramuscularly at a dosage of 5 mg of octreotide per kg of body weight exhibits an octreotide concentration of at least 0.3 ng/ml and at most 20 ng/ml during a 50 day term.

6. A sustained release formulation according to claim 3 which when administered to a rabbit intramuscularly at a dosage of 5 mg of octreotide per kg of body weight exhibits a retardation of at least 70% over a period of from 0 to 42 or 43 days.

7. A sustained release formulation according to claim 3 which when administered to a rat subcutaneously at a dosage of 10 mg of octreotide per kg of body weight exhibits an average plasma level of from 2.5 to 6.5 ng/ml over a period of from 0 to 42 days.

8. A sustained release formulation according to claim 3 which when administered to a rabbit intramuscularly at a dosage of 5 mg of octreotide per kg of body weight exhibits an average plasma level of from 3.5 to 6.5 ng/ml.

9. A microparticle according to claim 2 wherein the octreotide is in pamoate salt form.

10. A sustained release formulation comprising a microparticle of claim 9.

11. A microparticle according to claim 2 wherein the surface is substantially free of octreotide.

12. A sustained release formulation comprising a microparticle of claim 1.

13. A microparticle of claim 1 wherein said octreotide is an acetate salt.

* * * * *